United States Patent
Fujita et al.

(10) Patent No.: US 11,963,778 B2
(45) Date of Patent: Apr. 23, 2024

(54) BELT AND ELECTROCARDIOGRAM MEASUREMENT DEVICE

(71) Applicants: OMRON HEALTHCARE Co., Ltd., Kyoto (JP); OMRON Corporation, Kyoto (JP)

(72) Inventors: Reiji Fujita, Kyoto (JP); Yasuhiro Kawabata, Kyoto (JP); Kenji Fujii, Kyoto (JP); Naomi Matsumura, Kyoto (JP); Akito Ito, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 559 days.

(21) Appl. No.: 17/139,380

(22) Filed: Dec. 31, 2020

(65) Prior Publication Data

US 2021/0121114 A1    Apr. 29, 2021

Related U.S. Application Data

(63) Continuation of application No. PCT/JP2019/026083, filed on Jul. 1, 2019.

(30) Foreign Application Priority Data

Jul. 6, 2018 (JP) ................. 2018-129400

(51) Int. Cl.
*A61B 5/282* (2021.01)
*A61B 5/00* (2006.01)

(52) U.S. Cl.
CPC ............ *A61B 5/282* (2021.01); *A61B 5/0006* (2013.01)

(58) Field of Classification Search
CPC ......... A61B 5/282; A61B 5/0006; A61B 5/25; A61B 5/251; A61B 5/256; A61B 5/28
See application file for complete search history.

(56) References Cited

U.S. PATENT DOCUMENTS 5,865,741 A * 2/1999 Kelly ................ A61B 5/282
600/386
2003/0187363 A1 10/2003 Alroy
(Continued)

FOREIGN PATENT DOCUMENTS

| CN | 1426287 A | 6/2003 |
| CN | 103607945 A | 2/2014 |

(Continued)

OTHER PUBLICATIONS

International Preliminary Report on Patentability and Written Opinion of the International Searching Authority dated Jan. 12, 2021 in International (PCT) Application No. PCT/JP2019/026083.
(Continued)

*Primary Examiner* — Adam Z Minchella
(74) *Attorney, Agent, or Firm* — Wenderoth, Lind & Ponack, L.L.P.

(57) ABSTRACT

A belt and electrocardiographic measurement device, the belt including a belt body windable around an upper arm in a circumferential direction of the upper arm, and an electrode array including a plurality of electrodes fixed to an inner surface of the belt body and arranged side by side in a direction, which is a longitudinal direction of the belt body, the plurality of electrodes being more than N+2 in number, where N is a number of electrodes required for obtaining electrocardiographic information, the electrodes, counted from a first electrode located at a first end in the direction (X) by counting including the first electrode, to the (N+1)th electrode in the direction (X) being arranged at equal intervals that are predetermined intervals, and intervals between (Continued)

each of the (N+1)th and subsequent electrodes being greater than the predetermined interval.

5 Claims, 6 Drawing Sheets

(56) References Cited

U.S. PATENT DOCUMENTS

2014/0081118 A1   3/2014  Reinhold, Jr. et al.
2019/0183369 A1*  6/2019  Shakur ................ A61B 5/6823

FOREIGN PATENT DOCUMENTS

| | | |
|---|---|---|
| CN | 205649496 | 10/2016 |
| JP | 2003-527185 A | 9/2003 |
| JP | 5428889 B2 | 2/2014 |
| JP | 2014-517759 A | 7/2014 |
| JP | 2016-158709 A | 9/2016 |
| WO | 0170101 A2 | 9/2001 |
| WO | 2012/160550 A1 | 11/2012 |

OTHER PUBLICATIONS

Notice of First Examination Opinion dated Jul. 24, 2023 in corresponding Chinese Patent Application No. 201980038362.0, with English language translation.

* cited by examiner

[FIG. 1]
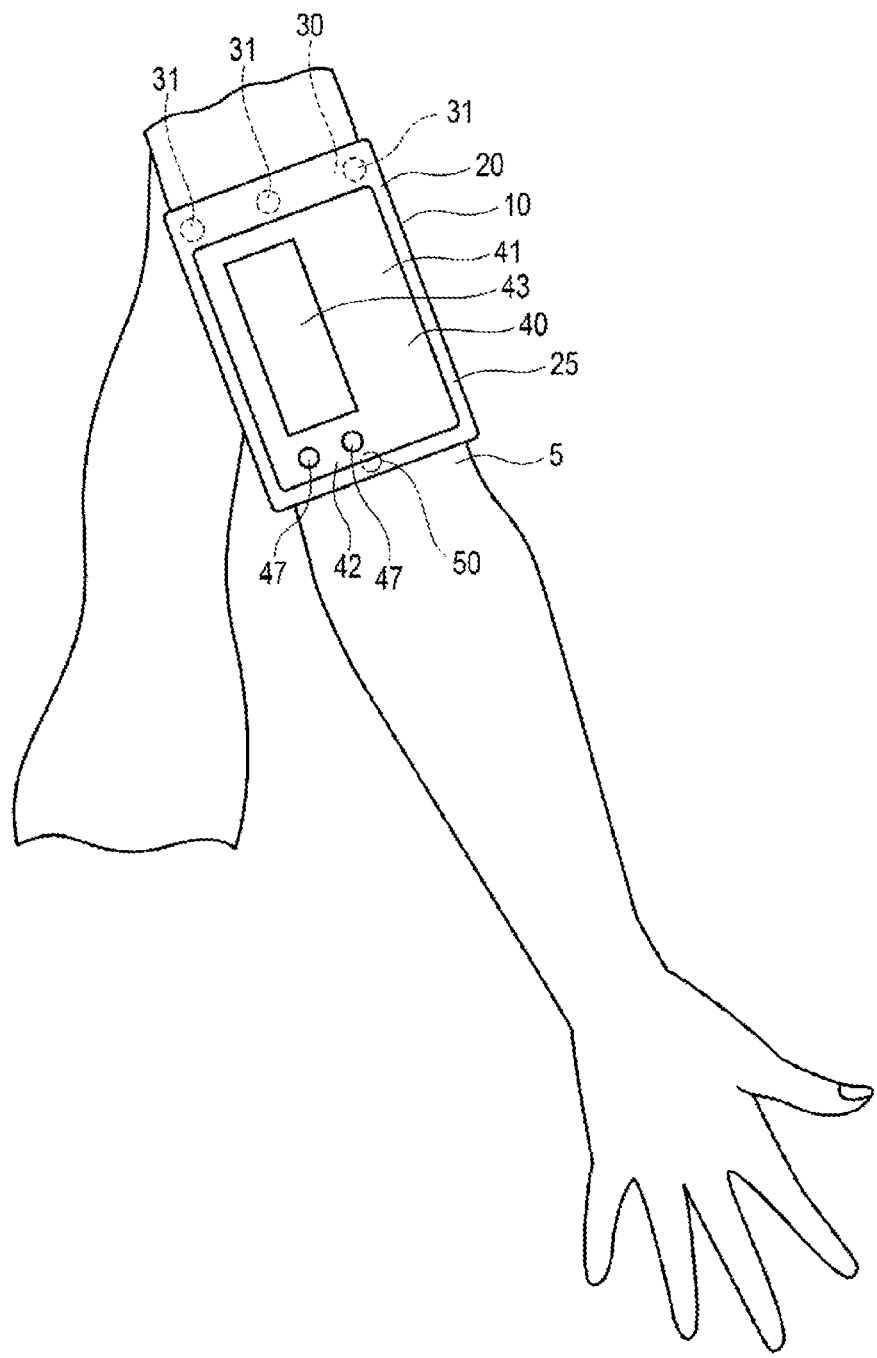

[FIG. 2]
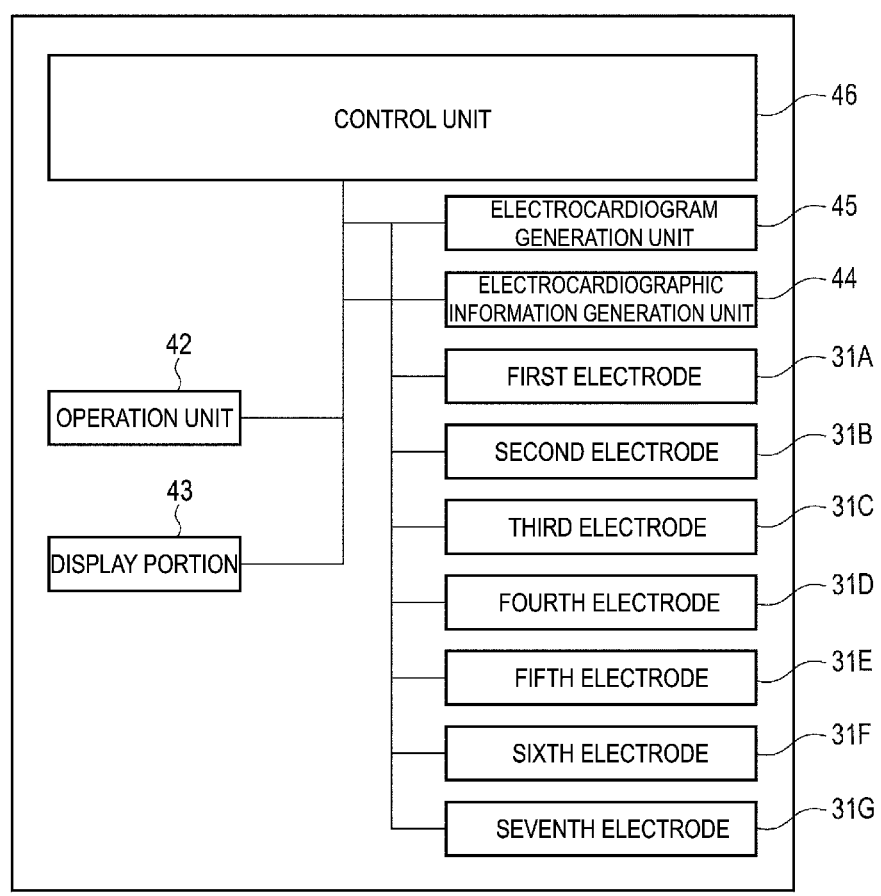

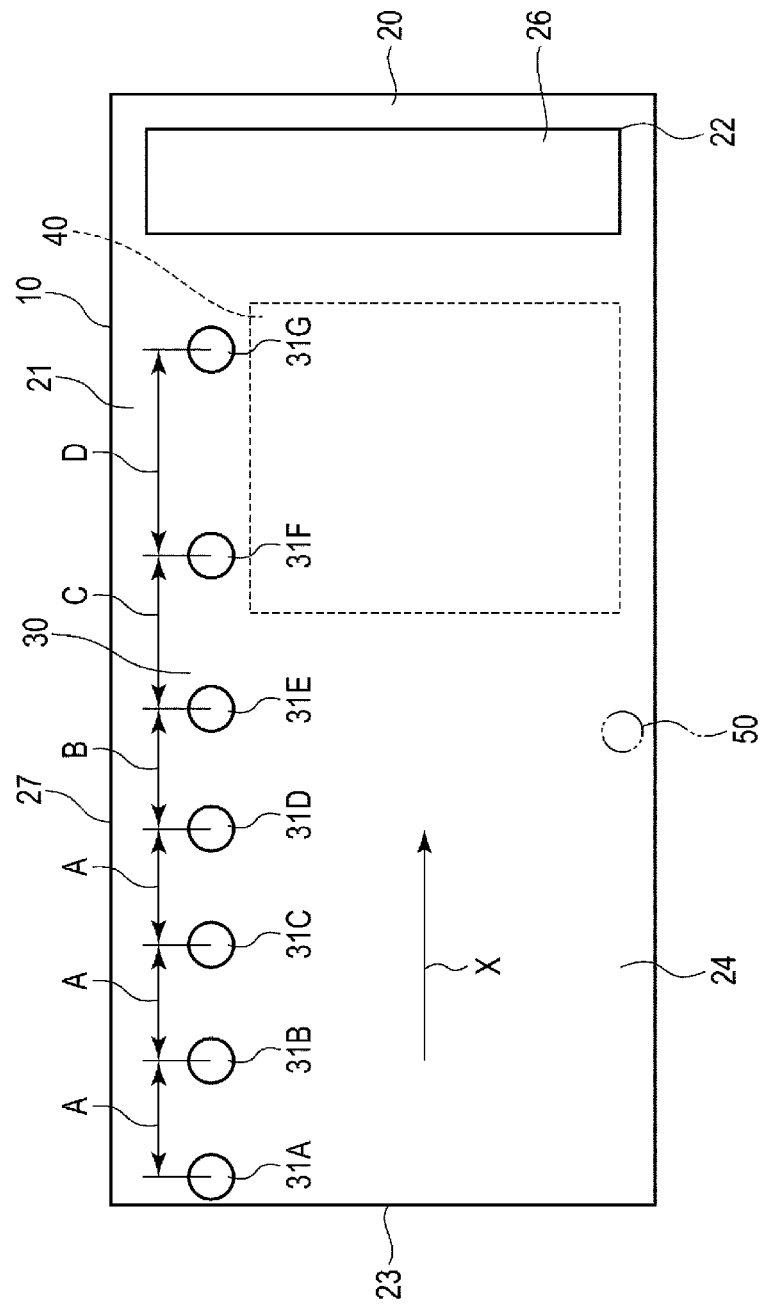

[FIG. 4]
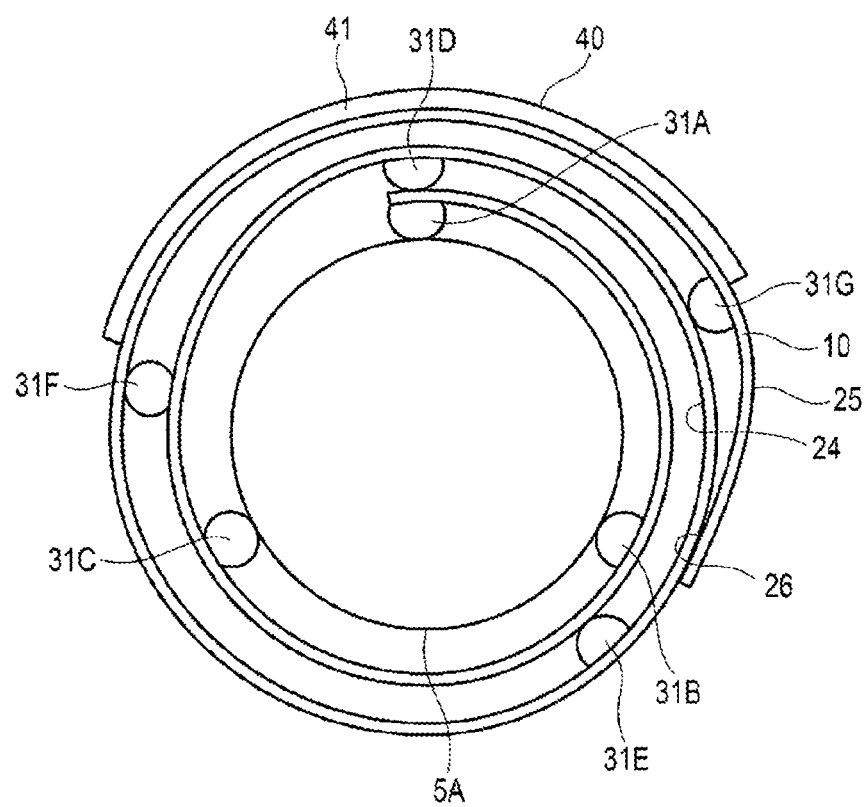

[FIG. 5]
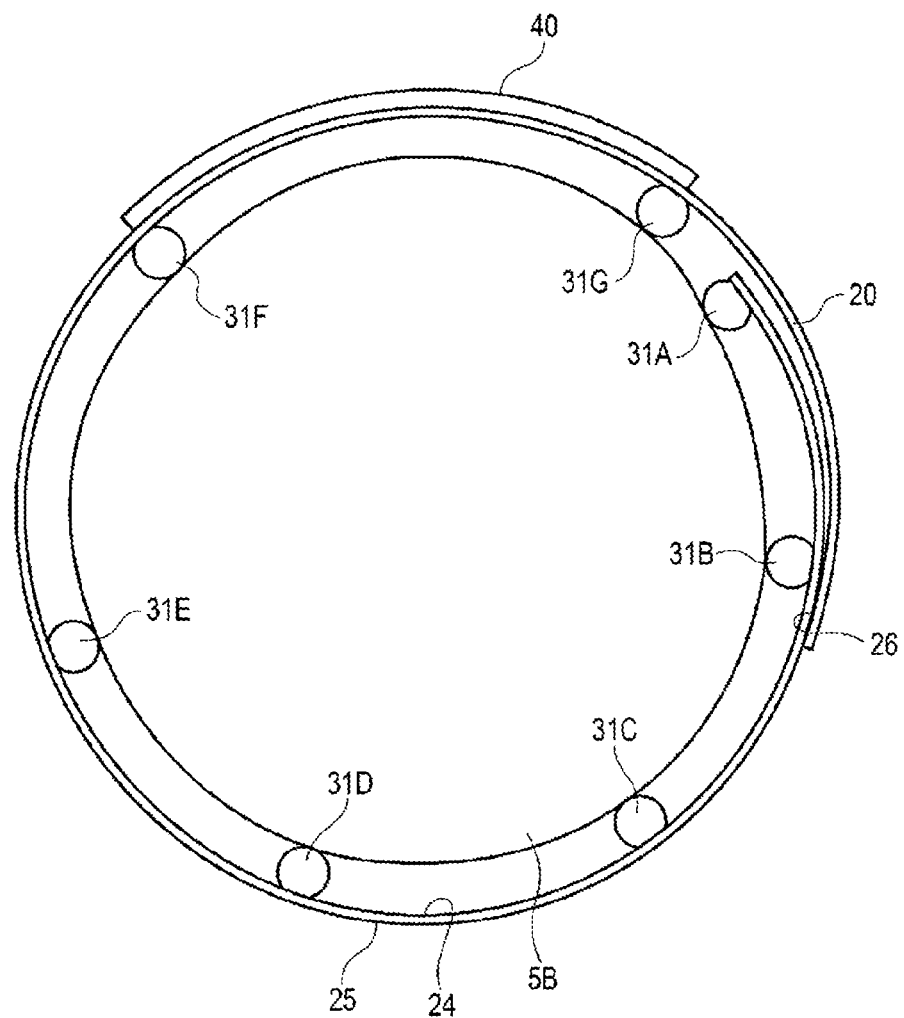

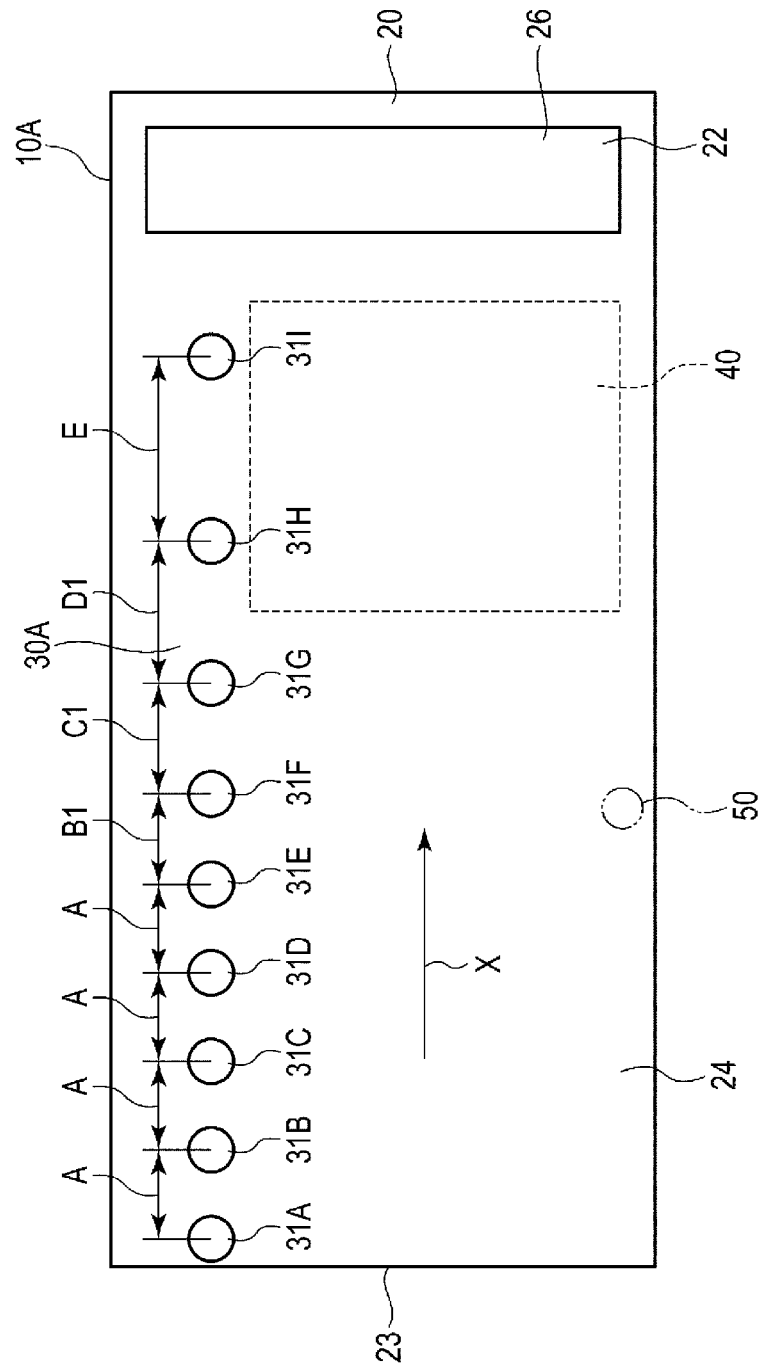

BELT AND ELECTROCARDIOGRAM MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/026083, filed Jul. 1, 2019, which application claims priority from Japanese Patent Application No. 2018-129400, filed Jul. 6, 2018, which applications are incorporated herein by reference in their entireties.

TECHNICAL FIELD

The present invention relates to a belt and an electrocardiographic measurement device that outputs signals corresponding to electric potential at a surface of a living body caused by cardiac activity.

BACKGROUND ART

A known electrocardiograph measures the electrocardiographic waveform of a user by detecting voltage at the surface of the skin of a living body caused by cardiac activity.

An example of such a known electrocardiograph (for example, see Patent Document 1) is provided with a belt that includes belt body that is wound around an upper arm of a user and a plurality of electrodes fixed to an inner surface of the belt body at equal intervals in one direction.

CITATION LIST

Patent Literature

Patent Document 1: JP 5428889 B

SUMMARY OF INVENTION

Technical Problem

An electrocardiographic measurement device including a plurality of electrodes fixed on an inner surface of a belt at equal intervals includes those many electrodes to accommodate for the upper arm of various users. That is, since the length in the circumferential direction of the upper arm is different depending on the user, many electrodes are required to accommodate upper arms having different lengths in the circumferential direction. Thus, the circuit for creating the electrocardiographic waveform on the basis of the output from the electrodes is complex.

In light of this, an object of the present invention is to provide a belt and an electrocardiographic measurement device in which a large number of electrodes does not need to be provided.

Solution to Problem

According to an aspect, provided is a belt including, a belt body windable around a living body in a circumferential direction of the living body, and an electrode array including a plurality of electrodes fixed to an inner surface of the belt body facing the living body and arranged side by side in a longitudinal direction of the belt body, the plurality of electrodes being more than N+2 in number, where N is a number of electrodes required for obtaining electrocardiographic information, the electrodes, counted from the electrode located at a first end in an arrangement direction by counting including this electrode, to the (N+1)th electrode in the arrangement direction being arranged at equal intervals that are predetermined intervals, and intervals between each of the (N+1)th and subsequent electrodes being greater than the predetermined interval.

Here, the living body is an upper arm, for example. "Counted from the electrode located at a first end in an arrangement direction by counting including this electrode" means that the electrode disposed at the first end is counted as the first electrode.

According to this aspect, with a small number of electrodes, the electrodes are disposed at positions with intervals of approximately 1/N of the circumferential length in the circumferential direction of the living body. In this way, a large number of electrodes does not need to be provided.

In the belt according to the aspect described above, the intervals in the arrangement direction between each of the (N+1)th and subsequent electrodes increase as the ordinal number of the electrode counted from the electrode located at the first end in the arrangement direction increases where (N+1)th is counted from the electrode located at the first end in the arrangement direction by counting including this electrode.

According to this aspect, a large number of electrodes does not need to be provided.

In the belt according to the aspect described above, a distance from the electrode located at the first end in the arrangement direction to each of the (N+2)th and subsequent electrodes, where (N+2)th is counted from the electrode located at the first end by counting including this electrode, is (N−1)/N×L, where L is a maximum length of an adaptive circumferential length.

Here, the circumferential length is the adaptive circumferential length for each of the (N+2)th and subsequent electrodes, from among the used electrodes, when the ordinal number in the arrangement direction counted from the electrode located at the first end by counting including this electrode is highest. Here, the plurality of electrodes used correspond to the electrodes that are in contact with the skin of the living body. For example, "up to the fifth electrode counted from the first end are used" means that the first to fifth electrodes, i.e., 5 electrodes, are in contact with the living body, and the sixth and subsequent electrodes are in contact with the outer surface of the wound belt.

In case in which the electrode located at the first end is counted as the first electrode and the electrode farthest in the arrangement direction from the first electrode is the fifth electrode, for example, the adaptive circumferential length of the living body when each of the (N+2)th and subsequent electrodes is the electrode farthest in the arrangement direction from the electrode located at the first end from among the plurality of used electrodes is, when the belt is wound around the living body, equal to or greater than the circumferential length of the living body with the fifth electrode disposed at a position adjacent to the first electrode in the circumferential direction of the living body, and equal to or less than the circumferential length of the living body with the sixth electrode disposed at a position facing the first electrode in the direction orthogonal to the circumferential direction of the living body. In this case, the maximum length is a circumferential length in which the sixth electrode is arranged next to the first electrode in the direction orthogonal to the circumferential direction of the living body.

According to this aspect, with a small number of electrodes, the electrodes are disposed at positions at intervals of approximately 1/N of the circumferential length in the circumferential direction of the living body.

According to another aspect, provided is a electrocardiographic measurement device, including, a belt body windable around a living body in a circumferential direction of the living body, an electrode array including a plurality of electrodes fixed to an inner surface of the belt body facing the living body and arranged side by side in a longitudinal direction of the belt body, the plurality of electrodes being more than N+2 in number, where N is a number of electrodes required for obtaining electrocardiographic information, the electrodes, counted from the electrode located at a first end in an arrangement direction by counting including this electrode, to the (N+1)th electrode in the arrangement direction being arranged at equal intervals that are predetermined intervals, and intervals between each of the (N+1)th and subsequent electrodes being greater than the predetermined interval, and a processing unit configured to generate electrocardiographic information on the basis of output from the electrodes.

Here, the living body is an upper arm, for example. "Counted from the electrode located at a first end in an arrangement direction by counting including this electrode" means that the electrode located at the first end is counted as the first electrode.

According to this aspect, the electrocardiographic measurement device does not need to be provided with a large number of electrodes.

In the electrocardiographic measurement device according to the aspect described above, the processing unit calculates respective potential differences between a reference electrode, which is one of the plurality of electrodes, and other electrodes of the plurality of electrodes, and generates electrocardiographic information on the basis of a negative maximum value and a positive maximum value of calculation results.

According to this aspect, electrodes, other than the electrodes of the electrode array, for generating information required to generate an electrocardiogram are not needed. Thus, a large number of electrodes does not need to be provided.

Advantageous Effects of Invention

The present invention can provide a belt and an electrocardiographic measurement device in which a large number of electrodes does not need to be provided.

BRIEF DESCRIPTION OF DRAWINGS

FIG. 1 is a perspective view illustrating the configuration of an electrocardiographic measurement device according to an embodiment of the present invention.

FIG. 2 is a block diagram illustrating the configuration of the electrocardiographic measurement device.

FIG. 3 is an explanatory diagram schematically illustrating the configuration of the electrocardiographic measurement device.

FIG. 4 is an explanatory diagram illustrating an example of the electrocardiographic measurement device in use.

FIG. 5 is an explanatory diagram illustrating an example of the electrocardiographic measurement device in use.

FIG. 6 is an explanatory diagram schematically illustrating the configuration of an electrocardiographic measurement device according to another embodiment of the present invention.

DESCRIPTION OF EMBODIMENTS

An example of an electrocardiographic measurement device 10 according to an embodiment of the present invention is described below using FIGS. 1 to 5.

FIG. 1 is a perspective view illustrating the configuration of the electrocardiographic measurement device 10 with the electrocardiographic measurement device 10 worn by a user. FIG. 2 is a block diagram illustrating the configuration of the electrocardiographic measurement device 10. FIG. 3 is an explanatory diagram illustrating the electrocardiographic measurement device 10 with the belt 20 unfolded. FIGS. 4 and 5 are explanatory diagrams illustrating examples of the electrocardiographic measurement device 10 in use with the electrocardiographic measurement device 10 worn by a user.

The electrocardiographic measurement device 10 is an electrocardiographic measurement device that is mounted on an upper arm 5, for example, of a living body, detects the electric potential at a plurality of points on the surface of the skin of the upper arm 5, and generates information necessary for generating an electrocardiogram based on these detected voltages.

As illustrated in FIGS. 1 to 3, the electrocardiographic measurement device 10 includes a belt 20, an electrode array 30 fixed to the belt 20, and a device body 40 fixed to the belt 20.

The belt 20 includes a band-like belt body 21 and fixing member 22 for fixing the belt body 21 in a state of being wound around the upper arm 5. The belt 20 fixes the device body 40 to the upper arm 5.

As illustrated in FIGS. 4 and 5, the belt body 21 is wound around the upper arm 5 from a first end 23 in the longitudinal direction of the belt body 21. The belt body 21 includes an inner surface 24 that is disposed to face the upper arm 5 when the belt body 21 is wound around the upper arm 5 and an outer surface 25, which is the surface on the side opposite the inner surface 24. The device body 40 is fixed to the outer surface 25 at the other end portion in the longitudinal direction.

The fixing member 22, for example, is a surface fastener. The fixing member 22 includes a loop provided on the, for example, entire surface of the outer surface 25 and a hook 26 provided on the inner surface 24 at the other end portion in the longitudinal direction. The belt 20 is fixed to the upper arm 5 by the belt 20 being wrapped around the upper arm 5 in the circumferential direction and the hook 26 engaging with the loop.

As illustrated in FIG. 3, the electrode array 30 is provided on the inner surface 24. The electrode array 30 is provided, for example, on the inner surface 24 closer to an edge 27 that is along the longitudinal direction of the inner surface 24, the edge 27 is closer to the shoulder when the belt 20 is worn on the upper arm 5.

The electrode array 30 includes a plurality of electrodes 31. The plurality of electrodes 31 are disposed in the longitudinal direction of the belt 20 from one end in the longitudinal direction of the inner surface 24. The electrode array 30 includes the plurality of electrodes 31 more than N+2 in number, where N is the minimum number of electrodes 31 required to be used to generate an electrocardiogram.

In the present embodiment, an electrocardiogram is generated based on the detection values of at least three electrodes 31 by an electrocardiographic information generation unit 44, which will be described later. In other words, N=3. Thus, in the present embodiment, the electrode array 30 includes seven electrodes 31, as an example of a number greater than five.

Of the plurality of electrodes 31, the electrode 31 fixed to the first end 23 in the longitudinal direction of the inner surface 24 of the belt 20 is defined as a first electrode 31A. Of the plurality of electrodes 31, the electrode 31 disposed on the other end with respect to the first electrode 31A in the arrangement direction is defined as a seventh electrode 31G.

The electrodes 31 between the first electrode 31A and the seventh electrode 31G are a second electrode 31B, a third electrode 31C, a fourth electrode 31D, a fifth electrode 31E, and a sixth electrode 31F in order from the side where the first electrode 31A is located.

The signal lines are respectively connected to the first to seventh electrodes 31A, 31B, 31C, 31D, 31E, 31F and 31G. The first to seventh electrodes 31A, 31B, 31C, 31D, 31E, 31F and 31G output, via the signal lines, signals corresponding to the electric potential at sections of the skin of the upper arm 5 in contact with the electrodes.

The first to seventh electrodes 31A, 31B, 31C, 31D, 31E, 31F and 31G have an arrangement structure which satisfies the following conditions 1 to 4, where N is the minimum number of electrodes used to generate the information required to generate an electrocardiogram.

Condition 1 is a condition that: the electrodes up to the (N+1)th electrode, as counted from the first electrode 31A by counting including the first electrode 31A, are arranged at equal intervals in one direction of the arrangement direction of the electrodes 31, this direction in the present embodiment being a direction X from the first end 23 of the belt body 21 toward the other end. Note that "counted from the first electrode 31A by counting including the first electrode 31A" means that the first electrode 31A is counted as the first electrode.

In other words, the electrodes from the first electrode 31A to the fourth electrode 31D are arranged side by side at a predetermined pitch width A. The pitch width A is set, for example, to one third of the circumferential length of the upper arm of a user who has the thinnest upper arm assumed for the electrocardiographic measurement device 10.

Condition 2 is a condition that: the intervals between each of the (N+1)th and subsequent electrodes, counted in the direction X from the first electrode 31A by counting including the first electrode 31A, are greater than the pitch width A.

In other words, a pitch width B between the fourth electrode 31D and the fifth electrode 31E is greater than the pitch width A. A pitch width C between the fifth electrode 31E and the sixth electrode 31F is greater than the pitch width A. A pitch width D between the sixth electrode 31F and the seventh electrode 31G is greater than the pitch width A.

Condition 3 is a condition that: the intervals between each of the (N+1)th and subsequent electrodes, counted in the direction X from the first electrode 31A by counting including the first electrode 31A, increases as the electrodes are located farther from the first electrode 31A in the direction X. In other words, the pitch width A< the pitch width B< the pitch width C< the pitch width D holds true.

Condition 4 is a condition that: the distance in the direction X from the first electrode 31A to each of the (N+2)th and subsequent electrodes 31, counted from the first electrode 31A by counting including the first electrode 31A, is $(N-1)/N \times L$, where L is the maximum length of the adaptive circumferential length of the upper arm 5 when each of the (N+2)th and subsequent electrodes 31 is the electrode 31 farthest in the direction X from the first electrode 31A from among the plurality of electrodes 31 used.

Note that the plurality of electrodes 31 used corresponds to the electrodes that are in contact with the skin of the upper arm 5. For example, "electrodes 31 up to the fifth electrode 31E are used" means that the first to fifth electrodes 31A, 31B, 31C, 31D and 31E are in contact with the skin of the upper arm 5 and the sixth and seventh electrodes 31F and 31G are in contact with the outer surface 25 of the wound belt 20.

"The adaptive circumferential length of the upper arm 5 when each of the (N+2)th and subsequent electrodes 31 is the electrode farthest in the direction X from the first electrode 31A from among the plurality of electrodes 31 used" means, for each electrode, the circumference of the arm where the next electrode is not in use.

For example, in the case in which the electrode farthest in the direction X from the first electrode 31A is the fifth electrode 31E, the length is equal to or greater than the circumferential length of the upper arm 5 with the fifth electrode 31E disposed at a position adjacent to the first electrode 31A in the circumferential direction of the upper arm 5, when the belt 20 is wound around the upper arm 5, and the length is equal to or less than the circumferential length of the upper arm 5 with the sixth electrode 31F, which is the next electrode after the fifth electrode 31E in the direction X, disposed at a position facing the first electrode 31A in the direction orthogonal to the circumferential direction of the upper arm 5. In this case, the maximum length of the adaptive circumferential length is the circumferential length of the upper arm 5 that makes the sixth electrode 31F be disposed at a position opposite the first electrode 31A in the direction orthogonal to the circumferential direction of the upper arm 5.

In the present embodiment, the distance from the first electrode 31A to the fifth electrode 31E, which is (3A+B), is $\frac{2}{3} \times L1$, where L1 is the maximum value of the adaptive circumferential length of the upper arm 5 in the case in which the first to fifth electrodes 31A, 31B, 31C, 31D and 31E are used and the sixth and seventh electrodes 31F and 31G are not used. In other words, $B=(\frac{2}{3} \times L1)-(3 \times A)$.

The distance from the first electrode 31A to the sixth electrode 31F, which is (3×A+B+C), is $\frac{2}{3} \times L2$, where L2 is the maximum value of the adaptive circumferential length of the upper arm 5 in the case in which the first to sixth electrodes 31A, 31B, 31C, 31D, 31E and 31F are used and the seventh electrode 31G is not used. In other words, $C=(\frac{2}{3} \times L2)-(3 \times A)-B$.

The distance from the first electrode 31A to the seventh electrode 31G, which is (3×A+B+C+D), is $\frac{2}{3} \times L3$, where L3 is the maximum value of the adaptive circumferential length of the upper arm 5 in the case in which the first to seventh electrodes 31A, 31B, 31C, 31D, 31E, 31F and 31G are used. In other words, $D=(\frac{2}{3} \times L3)-(3 \times A)-B-C$.

Note that the adaptive circumferential length of the upper arm 5 and the maximum value for the adaptive circumferential length are predetermined.

The device body 40 includes a case 41, an operation unit 42, a display unit 43, an electrocardiographic information generation unit 44, an electrocardiogram generation unit 45, and a control unit 46.

The case 11 houses a portion of the operation unit 42, a portion of the display unit 43, and the control unit 46, and the electrocardiographic information generation unit 44, with a portion of the operation unit 42 and a portion of the display unit 43 being exposed from the outer surface.

The operation unit 42 is configured to receive a command input from a user. For example, the operation unit 42 includes a plurality of buttons 47 provided on the case 41 and a sensor that detects operation of the buttons 47. Note that the operation unit 42 may be provided on the display unit 43 as a touch panel. When the operation unit 42 is operated by the user, the operation unit 42 converts a command into an electrical signal. The sensor that detects operation of the buttons 47 is electrically connected to the control unit 46. The sensor that detects operation of the buttons 47 outputs an electrical signal to the control unit 46.

The display unit 43 is disposed in the case 41 exposed from the outer surface of the case 41. The display unit 43 is electrically connected to the control unit 46. The display unit 43 is, for example, a liquid crystal display or an organic electroluminescence display. The display unit 43 displays various information such as the date and time, an electrocardiogram.

The electrocardiographic information generation unit 44 is electrically connected to the plurality of electrodes 31 of the electrode array 30 via a signal line, for example. The electrocardiographic information generation unit 44 calculates the potential difference between a reference electrode, which is one of the plurality of electrodes 31, and another one of the plurality of electrodes 31. In the present embodiment, for example, the first electrode 31A is set as the reference electrode. In addition, the electrocardiographic information generation unit 44 generates the electrocardiographic information on the basis of the positive maximum value and the negative maximum value of the calculation result. The electrocardiographic information generation unit 44 is electrically connected to the electrocardiogram generation unit 45.

The electrocardiogram generation unit 45 generates information of the electrocardiogram on the basis of the electrocardiographic information generated by the electrocardiographic information generation unit 44. The electrocardiogram generation unit 45 is electrically connected to the control unit 46.

The control unit 46 is constituted by, for example, a single or a plurality of central processing units (CPU) and controls the entire operation of the electrocardiographic measurement device 10. The control unit 46 is electrically connected to the operation unit 42, the display unit 43, and the electrocardiographic information generation unit 44. The control unit 46 controls the operation of, transmits signals to and receives signals from, and supplies power to the operation unit 42, the display unit 43, the electrocardiographic information generation unit 44, and the electrocardiogram generation unit 45.

Next, the operation of the electrocardiographic measurement device 10 will be described. First, the user winds the belt 20 around the upper arm 5 as illustrated in FIG. 1. At this time, the user winds the belt 20 from the first end where the first electrode 31A of the belt 20 is disposed, as illustrated in FIGS. 4 and 5. When the belt 20 is wound around the upper arm 5, the user fixes the belt 20 with the fixing member 22.

FIG. 4 illustrates a state, as seen from the finger side, in which the electrocardiographic measurement device 10 is fixed to an upper arm 5A with a circumferential length being three times the length of the pitch width A. As illustrated in FIG. 4, the first electrode 31A, the second electrode 31B, and the third electrode 31C are in contact with the surface of the skin of the upper arm 5A. The first electrode 31A, the second electrode 31B, and the third electrode 31C are respectively located at positions dividing the circumferential length substantially into thirds in the circumferential direction of the upper arm 5A. The fourth electrode 31D and subsequent electrodes 31 are in contact with the outer surface 25 of the belt 20 wound around the upper arm 5A.

FIG. 5 illustrates a state, as seen from the finger side, in which the electrocardiographic measurement device 10 is worn on an upper arm 5B with a circumferential length equal to the length in which the first to seventh electrodes 31A, 31B, 31C, 31D, 31E, 31F and 31G are in contact with the surface of the skin. The first electrode 31A, the fourth electrode 31D, and the seventh electrode 31F are respectively located at positions approximately 1/N of the circumferential length, in other words, dividing the circumferential length substantially into thirds, in the circumferential direction of the upper arm 5B.

When the user fixes the electrocardiographic measurement device 10 to the upper arm 5 with the belt 20, the user starts measuring the electric potential by operating the operation unit 42.

When measurement of the electric potential starts, the electrodes in contact with the surface of the skin of the upper arm 5, from among the first to seventh electrodes 31A, 31B, 31C, 31D, 31E, 31F and 31G, output signals corresponding to the electric potential at sections where the electrodes are in contact with the skin to the electrocardiographic information generation unit 44.

In the electrocardiographic measurement device 10 worn on the upper arm 5A illustrated in FIG. 4, each of the first to third electrodes 31A, 31B and 31C output a signal corresponding to the electric potential to the electrocardiographic information generation unit 44. In the electrocardiographic measurement device 10 worn on the upper arm 5B illustrated in FIG. 5, each of the first to seventh electrodes 31A, 31B, 31C, 31D, 31E, 31F and 31G output a signal corresponding to the electric potential to the electrocardiographic information generation unit 44.

The electrocardiographic information generation unit 44 calculates the potential difference between the electrodes in contact with the upper arm 5, from among the second to seventh electrodes 31B, 31C, 31D, 31E, 31F and 31G with respect to the first electrode 31A on the basis of the information of the electric potential transmitted from the electrode array 30.

When the device is worn on the upper arm 5A illustrated in FIG. 4, the electrocardiographic information generation unit 44 calculates the potential difference between the first electrode 31A and the second electrode 31B and the potential difference between the first electrode 31A and the third electrode 31C.

When the device is worn on the upper arm 5B illustrated in FIG. 5, the electrocardiographic information generation unit 44 calculates the potential difference between the first electrode 31A and the second electrode 31B, the potential difference between the first electrode 31A and the third electrode 31C, the potential difference between the first electrode 31A and the fourth electrode 31D, the potential difference between the first electrode 31A and the fifth electrode 31E, the potential difference between the first electrode 31A and the sixth electrode 31F, and the potential difference between the first electrode 31A and the seventh electrode 31G.

When the potential differences are calculated, the electrocardiographic information generation unit 44 generates the electrocardiographic information on the basis of the positive maximum value and the negative maximum value of the calculation results. The electrocardiographic information is an example of information required to generate an electrocardiogram. The electrocardiographic information generation unit 44 transmits the generated information to the electrocardiogram generation unit 45.

The electrocardiogram generation unit 45 generates an electrocardiogram based on the information from the electrocardiographic information generation unit 44. The control unit 46 displays an electrocardiogram on the display unit 43 based on the information of the electrocardiogram generated by the electrocardiogram generation unit 45.

According to the electrocardiographic measurement device 10 configured in this manner, the plurality of electrodes 31 of the electrode array 30 are disposed in accordance with condition 1 and condition 2, so that, with a small number of electrode, the electrodes are disposed at positions at intervals of approximately 1/N of the circumferential length in the circumferential direction of the upper arm 5.

In other words, for a user with an upper arm 5 that has a short circumferential length, the first to third electrodes 31A, 31B and 31C disposed at equal intervals are disposed at positions that approximately divide the circumferential length into thirds in the circumferential direction of the upper arm 5. This allows the electrocardiographic information to be more accurately detected. For a user with an upper arm 5 that has a long circumferential length, any of the fourth electrode 31D and subsequent electrodes are respectively disposed at positions approximately ⅓ and approximately ⅔ of the circumferential length in the circumferential direction of the upper arm 5. This allows the electrocardiographic information to be more accurately detected. In other words, even with a small number of electrodes, any of the electrodes are disposed at positions at intervals of approximately 1/N of the circumferential length in the circumferential direction of the upper arm 5. In this way, a large number of electrodes does not need to be provided.

Furthermore, by disposing the plurality of electrodes 31 in accordance with condition 3, the number of electrodes 31 can be further reduced.

Furthermore, by disposing the plurality of electrodes 31 in accordance with condition 4, even with a small number of electrodes 31, any of the electrodes are disposed at positions at intervals of approximately 1/N of the circumferential length in the circumferential direction of the upper arm 5.

Furthermore, the electrocardiographic information generation unit 44 generates information on the basis of only the output of the plurality of electrodes 31 of the electrode array 30. Thus, electrodes, other than the electrodes 31 of the electrode array 30, for generating information required to generate an electrocardiogram are not needed. Thus, a large number of electrodes does not need to be provided.

Furthermore, the electrocardiographic measurement device 10 includes the electrocardiographic information generation unit 44, the electrocardiogram generation unit 45, and the display unit 43, allowing an electrocardiogram to be displayed on the display unit 43. Thus, the user can easily see the state of their own heart by viewing the display unit 43.

As described above, according to the electrocardiographic measurement device 10 of an embodiment of the present invention, a large number of electrodes does not need to be provided.

Note that the present invention is not limited to the embodiments described above. In the examples described above, the electrocardiographic measurement device 10 has a configuration in which the minimum value of the number of electrodes required to generate the electrocardiographic information is 3, but no such limitation is intended. In other examples, the minimum value of the number of electrodes required to generate the electrocardiographic information may be four. FIG. 6 illustrates the configuration of an electrocardiographic measurement device 10A, which is a modified example in which four electrodes are used to generate an electrocardiogram. As illustrated in FIG. 6, an electrode array 30A of the electrocardiographic measurement device 10A includes nine electrodes 31, for example.

The electrode 31 fixed at one end on the opposite side to the first electrode 31A in the arrangement direction of the plurality of electrodes 31 is defined as a ninth electrode 31I, and the second to eighth electrodes 31B, 31C, 31D, 31E, 31F, 31G and 31H are arranged between the first electrode 31A and the ninth electrode 31I.

The electrodes from the first electrode 31A to the fifth electrode 31E are arranged side by side at the predetermined pitch width A at equal intervals. A pitch width B1 between the fifth electrode 31E and the sixth electrode 31F, a pitch width C1 between the sixth electrode 31F and the seventh electrode 31G, a pitch width D1 between the seventh electrode 31G and the eighth electrode 31H, and a pitch width E between the eighth electrode 31H and the ninth electrode 31I are different. Furthermore, the pitch widths B1, C1, D1, and E are different from the pitch width A. Furthermore, $A<B1<C1<D1<E$ holds true.

Also, the pitch width B1 is $B1=(\frac{3}{4} \times L4)-(4 \times A)$, where L4 is the maximum length of the adaptive circumferential length of the upper arm 5 using up to the sixth electrode 31F. The pitch width C1 is $C1=(\frac{3}{4} \times L5)-(4 \times A)-B1$, where L5 is the maximum length of the adaptive circumferential length of the upper arm 5 using up to the seventh electrode 31G. The pitch width D1 is $D1=(\frac{3}{4} \times L6)-(4 \times A)-B1-C1$, where L6 is the maximum length of the adaptive circumferential length of the upper arm 5 using up to the eighth electrode 31H. The pitch width E is $E=(\frac{3}{4} \times L7)-(4 \times A)-B1-C1-D1$, where L7 is the maximum length of the adaptive circumferential length of the upper arm 5 using up to the ninth electrode 31I.

Also, in the examples described above, the electrocardiographic measurement devices 10 and 10A have a configuration in which an electrocardiogram is generated, but no such limitation is intended. For example, as illustrated by the two-dot dashed lines in FIGS. 1, 3, and 6, a pulse wave sensor 50 for detecting a user's pulse wave may be provided. In configurations including the pulse wave sensor 50, the position of the pulse wave sensor 50 with respect to the electrode array 30 is preferably a position where the pulse wave sensor 50 is located at the user's peripheral side with respect to the electrode array 30 when the electrocardiographic measurement devices 10 and 10A are worn on the upper arm 5. That is, the pulse wave sensor 50 is preferably located further away from the heart of the user than the electrode array 30 when the device is worn. Furthermore, in the case of a configuration including the pulse wave sensor 50, the control unit 46 may measure the pulse transit time (PTT) on the basis of the electrocardiographic waveform and the pulse waveform. The display unit 43 may display a pulse wave waveform.

Additionally, the electrocardiographic measurement devices 10 and 10A may include a blood pressure measurement device capable of measuring blood pressure. An example of a configuration capable of measuring blood pressure is a configuration that measures blood pressure by the oscillometric method.

In this example, the belt 20 includes, for example, an inner cloth, an outer cloth, and a pressing cuff provided between the inner cloth and the outer cloth. The pressing cuff is a long band extending in a longitudinal direction of the belt 20 that can encircle the upper arm. In this example, the pressing cuff is configured as a fluid bag by causing two stretchable polyurethane sheets to face each other in the thickness direction and welding the edge portions of the sheets. The electrode array 30 is provided on the inner cloth so as to be positioned between the pressing cuff and the upper arm 5 in the worn state.

Also, in the example described above, the electrocardiographic measurement devices 10 and 10A are worn on the upper arm 5 of the user, but no such limitation is intended. The electrocardiographic measurement devices 10 and 10A may be worn on the wrist of the user, for example.

Additionally, in the present embodiment, the electrocardiographic measurement devices 10 and 10A include the electrocardiogram generation unit 45 and the display unit 43 and is configured so that an electrocardiogram can be displayed to a user. However, no such limitation is intended. The electrocardiographic measurement devices 10 and 10A may have a configuration not including the display unit 43, for example. In this case, the electrocardiogram generation unit 45 of the electrocardiographic measurement devices 10 and 10A may be connected to another display device, and the electrocardiogram generation unit 45 may display an electrocardiogram on this display device. Alternatively, the electrocardiogram generation unit 45 may not be provided. In this case, the electrocardiographic information may be displayed as numerical values on the display unit 43 based on the information generated by the electrocardiographic information generation unit 44.

Additionally, as described above, in a case of a configuration capable of measuring the PTT and a configuration capable of measuring the blood pressure, blood pressure may be estimated from the PTT, and the blood pressure measurement device may measure blood pressure when the estimated value exceeds a preset threshold.

Alternatively, the electrocardiographic measurement devices 10 and 10A may have a configuration that does not include the electrocardiogram generation unit 45 and the display unit 43. In this case, the electrocardiographic information generation unit 44 of the electrocardiographic measurement devices 10 and 10A is connected to the other device that includes an electrocardiogram generation unit and a display unit, and the electrocardiographic information generation unit 44 may transmit information to the electrocardiogram generation unit of the other device.

Also, in the present embodiment, the plurality of electrodes 31 of the electrode array 30 have an arrangement structure that satisfies the conditions 1 to 4. However, the arrangement structure may only satisfy conditions 1 and 2, or the arrangement structure may satisfy conditions 1 and 2 as well as satisfy at least one of condition 3 and condition 4. In other words, the arrangement structure may satisfy conditions 1 and 2, conditions 1 to 3, or conditions 1, 2, and 4.

In this case, a similar effect can be obtained.

Also, the electrocardiographic measurement device 10 may be configured so that the belt 20 can be replaced. That is, the belt 20 may be configured such that the belt 20 can be replaced with a new belt 20 when the belt is damaged or reaches a replacement period.

Also, in the example described above, the electrocardiographic information is generated on the basis of the output of the electrodes 31 of the belt 20, but no such limitation is intended. The belt 20 can be used in a device that measures a state of the user on the basis of the output corresponding to electric potential.

Note that the present invention is not limited to the embodiment, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

REFERENCE SIGNS LIST

5 Upper arm
5A Upper arm
5B Upper arm
10 Electrocardiographic measurement device
10A Electrocardiographic measurement device
20 Belt
21 Belt body
22 Fixing member
30 Electrode array
30A Electrode array
31 Electrode
31A First electrode
31B Second electrode
31C Third electrode
31D Fourth electrode
31E Fifth electrode
31F Sixth electrode
31G Seventh electrode
31H Eighth electrode
31I Ninth electrode
40 Device body
41 Case
42 Operation unit
43 Display unit
44 Electrocardiographic information generation unit
45 Electrocardiogram generation unit
46 Control unit
47 Button
50 Pulse wave sensor
A Pitch width
B Pitch width
B1 Pitch width
C Pitch width
C1 Pitch width
D Pitch width
D1 Pitch width
E Pitch width

The invention claimed is:

1. A belt for an electrocardiographic measurement device configured to generate electrocardiographic information based on potentials detected at a plurality of portions of an upper arm, the belt comprising:
a belt body windable around the upper arm in a circumferential direction of the upper arm; and an electrode array including a plurality of electrodes fixed to an inner surface of the belt body to face the upper arm and arranged side by side in a longitudinal direction of the belt body, wherein the plurality of electrodes is more than N+2 in number, where N is a number of electrodes required for obtaining electrocardiographic information, the electrodes, counted from an electrode located at a first end in an arrangement direction by counting including this electrode, to an (N+1)th electrode in the arrangement direction are arranged at equal intervals that is a predetermined interval, intervals between each of the (N+1)th and subsequent electrodes are greater than the predetermined interval, N is equal to or greater than 3, and the predetermined interval of the electrodes up to the (N+1)th electrode is set to be 1/N of a circumferential length of an upper arm of a user among a plurality of users who are assumed to wear the electrocardiographic measurement device.

2. The belt according to claim 1, wherein the intervals in the arrangement direction between each of the (N+1)th and subsequent electrodes, where (N+1)th is counted from the electrode located at the first end in the arrangement direction by counting including this electrode, increase as the ordinal number of the electrode counted from the electrode located at the first end in the arrangement direction increases.

3. The belt according to claim 2, wherein a distance from the electrode located at the first end in the arrangement direction to each of (N+2)th and subsequent electrodes, where (N+2)th is counted from the electrode located at the first end by counting including this electrode, is $((N-1)/N) \times L_i$, where $L_i$ is a maximum length of an adaptive circumferential length of the (N+2)th and subsequent electrodes.

4. An electrocardiographic measurement device comprising:

a belt body windable around an upper arm in a circumferential direction of the upper arm;

an electrode array including a plurality of electrodes fixed to an inner surface of the belt body to face the upper arm and arranged side by side in a longitudinal direction of the belt body; and at least one processor configured to generate electrocardiographic information based on output from the electrodes, wherein the plurality of electrodes is more than N+2 in number, where N is a number of electrodes required for obtaining electrocardiographic information, the electrodes, counted from an electrode located at a first end in an arrangement direction by counting including this electrode, to an (N+1)th electrode in the arrangement direction are arranged at equal intervals that is a predetermined interval, intervals between each of the (N+1)th and subsequent electrodes are greater than the predetermined interval, N is equal to or greater than 3, and the predetermined interval of the electrodes up to the (N+1)th electrode is set to be 1/N of a circumferential length of an upper arm of a user among a plurality of users who are assumed to wear the electrocardiographic measurement device.

5. The electrocardiographic measurement device according to claim 4, wherein the at least one processor calculates respective potential differences between a reference electrode, which is one of the plurality of electrodes, and other electrodes of the plurality of electrodes, and generates the electrocardiographic information based on a negative maximum value and a positive maximum value of calculation results.

* * * * *